(12) United States Patent
Winter

(10) Patent No.: US 9,540,730 B2
(45) Date of Patent: Jan. 10, 2017

(54) DEPOSITION OF METAL FILMS BASED UPON COMPLEMENTARY REACTIONS

(71) Applicant: WAYNE STATE UNIVERSITY, Detroit, MI (US)

(72) Inventor: Charles H. Winter, Bloomfield Hills, MI (US)

(73) Assignee: WAYNE STATE UNIVERSITY, Detroit, MI (US)

( * ) Notice: Subject to any disclaimer, the term of this patent is extended or adjusted under 35 U.S.C. 154(b) by 0 days.

(21) Appl. No.: 14/430,282

(22) PCT Filed: Sep. 23, 2013

(86) PCT No.: PCT/US2013/061153
§ 371 (c)(1),
(2) Date: Mar. 23, 2015

(87) PCT Pub. No.: WO2014/047544
PCT Pub. Date: Mar. 27, 2014

(65) Prior Publication Data
US 2015/0247240 A1    Sep. 3, 2015

Related U.S. Application Data

(60) Provisional application No. 61/704,043, filed on Sep. 21, 2012.

(51) Int. Cl.
C23C 16/455    (2006.01)
C07F 19/00    (2006.01)
C23C 16/06    (2006.01)

(52) U.S. Cl.
CPC ......... *C23C 16/45553* (2013.01); *C07F 19/00* (2013.01); *C23C 16/06* (2013.01)

(58) Field of Classification Search
None
See application file for complete search history.

(56) References Cited

U.S. PATENT DOCUMENTS 6,099,903 A    8/2000    Kaloyeros et al.
6,538,147 B1    3/2003    Choi
(Continued)

FOREIGN PATENT DOCUMENTS

WO    2012027357    3/2012
WO    2013006242    1/2013
WO    2013188377    12/2013

OTHER PUBLICATIONS

Liu J Am Chem Soc 2001 V123 p. 8011-8021.*
(Continued)

*Primary Examiner* — Joseph Miller, Jr.
(74) *Attorney, Agent, or Firm* — Brooks Kushman P.C.

(57) ABSTRACT

A method comprises contacting a compound having formulae (1) with a compound having formula $ML_o$ to form a metal:

$$[M(SiR_3)_m(L_1)_p]_n \qquad (1)$$

wherein
M is Ti, V, Cr, Mn, Fe, Co, Ni, Cu, Zn, Al, a second row transition metal or a third row transition metal;
R are each independently H, $C_1$-$C_6$ alkyl or —Si(R")$_3$;
R" are each independently H or $C_1$-$C_6$ alkyl;
m is an integer from 1 to 3;
n is a number representing the formation of aggregates or polymeric material;
$L_1$ is a neutral donor ligand;
L is a ligand;
p is an integer from 0 to 6; and
o is an integer representing the number of ligands bonded to $ML_o$.

32 Claims, 2 Drawing Sheets

(56) References Cited

U.S. PATENT DOCUMENTS

| | | | |
|---|---|---|---|
| 6,984,591 B1 * | 1/2006 | Buchanan | C23C 16/16 257/751 |
| 8,148,564 B2 | 4/2012 | Winter | |
| 2008/0254218 A1 | 10/2008 | Lei et al. | |
| 2009/0104375 A1 | 4/2009 | Dussarrat et al. | |
| 2010/0239765 A1 | 9/2010 | Winter | |
| 2011/0068398 A1 * | 3/2011 | Anderson | H01L 21/2255 257/347 |
| 2012/0058270 A1 | 3/2012 | Winter et al. | |
| 2013/0164456 A1 | 6/2013 | Winter et al. | |
| 2013/0330473 A1 | 12/2013 | Winter et al. | |
| 2014/0161977 A1 | 6/2014 | Winter et al. | |
| 2014/0227444 A1 | 8/2014 | Winter et al. | |

OTHER PUBLICATIONS

Klein Inorganic Chimica Acta V177 No. 1 Nov. 1990 p. 35-42.*
International Search Report mailed Dec. 17, 2013 for PCT/US2013/061153, Filed Sep. 23, 2013, 3 pgs.

* cited by examiner

DEPOSITION OF METAL FILMS BASED UPON COMPLEMENTARY REACTIONS

CROSS-REFERENCE TO RELATED APPLICATIONS

This application is the U.S. national phase of PCT Application No. PCT/US2013/061153 filed Sep. 23, 2013, which claims the benefit of U.S. Provisional Application Ser. No. 61/704,043 filed Sep. 21, 2012, the disclosures of which are incorporated in their entirety by reference herein.

STATEMENT REGARDING FEDERALLY SPONSORED RESEARCH OR DEVELOPMENT

The invention was made with Government support under Contract No. CHE-1212574 awarded by the National Science Foundation. The Government has certain rights to the invention.

FIELD OF THE INVENTION

In at least one aspect, the present invention is related to the formation of metal films from "metalorganic" precursors.

BACKGROUND OF THE INVENTION

The growth of thin films is a central step in the fabrication of many functional materials and devices. While film growth efforts have been traditionally directed toward films greater than 100 nm, recent trends in several areas are calling for the growth of films ranging in thickness from a few atomic layers up to tens of nanometers.

In the microelectronics area, copper has replaced aluminum as the interconnect material in integrated circuits due to its lower resistivity and higher resistance to electromigration. Ultrathin (2-8 nm) manganese-silicon-oxygen layers have been proposed as replacements for existing nitride-based copper diffusion barrier layers in future devices. Since copper does not nucleate well on $SiO_2$ and other surfaces, it is difficult to deposit copper metal onto the surface features of microelectronic substrates. Accordingly, there has been considerable interest in the formation of seed layers of metals such as chromium, cobalt, and others which adhere better to substrates, and upon which copper films can be subsequently grown.

Atomic layer deposition ("ALD") is a thin film deposition technique that addresses many of the current technological demands. ALD affords inherently conformal coverage and sub-nanometer film thickness control due to its self-limited growth mechanism. In a typical ALD process, a substrate is contacted with a first chemical composition that modifies the substrate for a first predetermined period of time (a pulse). Such modification involves adsorption to the surface of the substrate, reaction with the surface of the substrate, or a combination of adsorption and reaction. A purging gas is introduced to remove any lingering first gaseous chemical composition in the vicinity of the substrate. A second gaseous chemical composition that reacts with the modified substrate surface is introduced for a second predetermined period of time into the vicinity of the substrate to form a portion of the thin film. A purging gas is subsequently introduced to remove any lingering second chemical composition in the vicinity of the substrate. These steps of contacting the substrate with the first chemical composition, purging, contacting the substrate with the second gaseous chemical composition, and purging are usually repeated a plurality of times until a film of desired thickness is coated onto the substrate. Although the prior art ALD processes work well, there is, unfortunately, only a limited number of chemical precursors having the requisite thermal stability, reactivity, and vapor pressure for ALD.

Accordingly, there is a need for improved methods for depositing thin films by atomic layer deposition.

SUMMARY OF THE INVENTION

The present invention solves one or more problems of the prior art by providing a method for forming a metal. The method comprises contacting a compound having formulae 1 with a compound having formula $ML_o$ to form a metal (i.e. zero oxidation state):

$$[M(Si(R_0)_3)_m(L_1)_p]_n \qquad 1$$

wherein
M is Ti, V, Cr, Mn, Fe, Co, Ni, Cu, Zn, Al, a second row transition metal or a third row transition metal;
$R_0$ are each independently H, $C_1$-$C_6$ alkyl or $-Si(R")_3$;
R" are each independently H or $C_1$-$C_6$ alkyl;
m is an integer from 1 to 6;
n is a number representing the formation of aggregates or polymeric material;
$L_1$ is a neutral donor ligand;
L is a ligand;
p is an integer from 0 to 6; and
o is an integer representing the number of ligands bonded to $ML_o$.

In another embodiment, a method of forming a metal film by an atomic layer deposition process is provided. The method comprises a deposition which includes contacting the substrate with vapor of a compound having formula 1 as set forth above such that at least a portion of the vapor of the compound having formula 1 adsorbs or reacts with a substrate surface to form a modified surface. The deposition cycle further includes contacting the modified surface with a vapor of a compound having formula $ML_o$ to react and form at least a portion of the metal film.

BRIEF DESCRIPTION OF THE DRAWINGS

Exemplary embodiments of the present invention will become more fully understood from the detailed description and the accompanying drawings, wherein.

DESCRIPTION OF THE INVENTION

Figure 1:
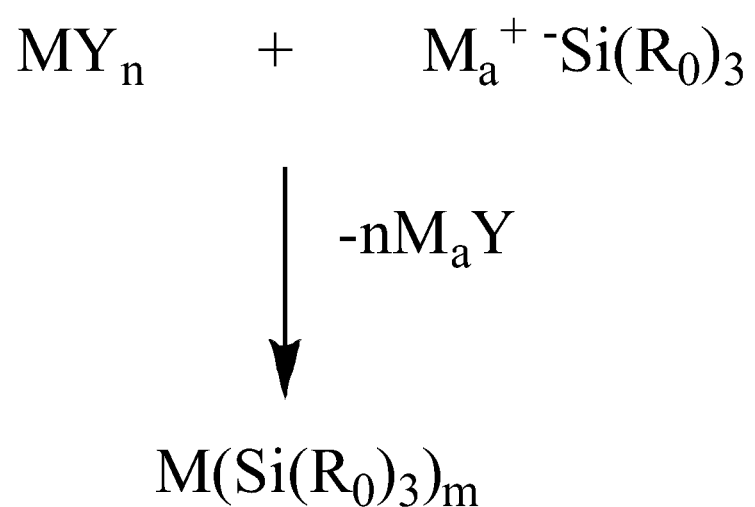
FIG. 1 is a flowchart showing the preparation of compounds having formula 1, 26, 27, and 28 where M is Ti, V, Cr, Mn, Fe, Co, Ni, Cu, Zn, a second row transition metal or a third row transition metal; $M_a$ is K, Na, Li, and the like; $R_0$ are each independently H, $C_1$-$C_6$ alkyl or $-Si(R")_3R'''$ are each independently H or $C_1$-$C_6$ alkyl; n is an integer from 1 to 6; and Y is a negatively charged counter-ion such as a halide.

Reference will now be made in detail to presently preferred compositions, embodiments and methods of the present invention which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

In an embodiment, a method for forming a metal is provided. The method comprises contacting a compound having formulae (1) with a compound having formula $ML_o$ to form a metal (e.g., metal atom in zero oxidation state):

$$[M(Si(R_0)_3)_m(L_1)_p]_n \qquad (1)$$

wherein
M is Ti, V, Cr, Mn, Fe, Co, Ni, Cu, Zn, Al, a second row transition metal or a third row transition metal;
$R_0$ are each independently H, $C_1$-$C_6$ alkyl or —Si(R")$_3$;
R" are each independently H or $C_1$-$C_6$ alkyl;
m is an integer from 1 to 6;
n is a number representing the formation of aggregates or polymeric material;
$L_1$ is a neutral donor ligand;
L is a ligand;
p is an integer from 0 to 6; and
o is an integer representing the number of ligands bonded to $ML_o$. It should be appreciated that each $R_0$ and R" bonded to an atom may be the same or different consistent with the choices set forth herein. Typically, L is a ligand that is more electronegative than M thereby polarizing the ML bond with a negative charge on L. It should be appreciated that a variety of different ligands may be used for L. For example, L can be a two electron ligand, a multidentate ligand (e.g., a bidentate ligand), charged ligand (e.g., −1 charged), a neutral ligand, and combinations thereof. In a refinement, m is from 1 to 3. Examples for neutral donor ligand $L_1$ include ethers, amines, phosphines, CO, $N_2$, and alkenes. Such neutral ligands may be derived from solvents (water, tetrahydrofuran, etc). In another refinement, o is an integer from 1 to 6. In another refinement, o is in increasing order of preference 2, 4, 6, 1, and 3. The reaction of the present embodiment is performed in the liquid or gas phase (e.g., chemical vapor deposition, ALD, et.) at temperatures from about 0 to 1000° C. In a refinement, the reaction is performed at temperatures from about 80 to 300° C. In another refinement, the reaction is performed at temperatures from about 150 to 300° C. In still another refinement, the reaction is performed at temperatures from about 200 to 250° C.

In general, M will be the same for the compound having formula 1 and for $ML_o$. In a refinement, $R_0$ and R" are each H, independently methyl, ethyl, n-propyl, isopropyl, n-butyl, sec-butyl, isobutyl, t-butyl and the like. In another refinement, n is a number from 1 to 1000 on average. In still another refinement, n is a number from 1 to 3 on average. Typically, n is 1. FIG. 1 provides a synthetic pathway for forming the compounds having formula 1.

In another refinement of the present embodiment, a method of making a copper film is provided. The method comprises contacting a compound having formulae 2 with a compound having formula $CuL_o$ to form a copper film:

$$[Cu(Si(R_0)_3)(L_1)_p]_n \qquad 2$$

wherein:
R are each independently H, $C_1$-$C_6$ alkyl or —Si(R')$_3$;
R' are each independently H or $C_1$-$C_6$ alkyl;
n is number representing the formation of aggregates or polymeric material; and
m is an integer representing the number of ligands bonded to $ML_o$. In a refinement, R and R' are each independently methyl, ethyl, propyl, n-butyl, sec-butyl, t-butyl, and the like. In another refinement, n is a number from 1 to 1000 on average. In still another refinement, n is a number from 1 to 3 on average. FIG. 1 provides a synthetic pathway for forming the compounds having formula 2.

In another refinement of the present embodiment, a method for forming a metal is provided. The method comprises contacting a compound selected from the group of compounds having formulae 3 with a compound having formula $ML_o$ to form a metal:

$$[M(Si(R_0)_3)_2]_n \qquad 3$$

wherein:
M is Co, Ti, V, Mn, Fe, Cr, Ni, Cu, Zn, a second transition metal, or a third row transition metal;
R are each independently H, $C_1$-$C_6$ alkyl or —Si(R")$_3$;
R" are each independently H or $C_1$-$C_6$ alkyl;
n is number representing the formation of aggregates or polymeric material; and
o is an integer representing the number of ligands bonded to $ML_o$. In a refinement, R and R' are each independently methyl, ethyl, propyl, n-butyl, sec-butyl, t-butyl, and the like. In another refinement, n is a number from 1 to 1000 on average. In still another refinement, n is a number from 1 to 3 on average. FIG. 1 provides a synthetic pathway for forming the compounds having formula 3.

In another refinement of the present embodiment, a method for forming a metal is provided. The method comprises contacting a compound selected from the group of compounds having formulae 4 with a compound having formula $ML_o$ to form a metal:

$$[M(Si(R_0)_3)_3]_n \quad 4$$

wherein:

M is V, Ti, Al, a second row transition metal, or a third row transition metal;

R are each independently H, $C_1$-$C_6$ alkyl or —Si(R")$_3$;

R" are each independently H or $C_1$-$C_6$ alkyl;

n is number representing the formation of aggregates or polymeric material; and o is an integer representing the number of ligands bonded to $ML_o$. In a refinement, R and R' are each independently methyl, ethyl, propyl, n-butyl, sec-butyl, t-butyl, and the like. In another refinement, n is a number from 1 to 1000 on average. In still another refinement, n is a number from 1 to 3 on average. Specific details for the present embodiment and for $ML_o$ are set forth in Appendix A. FIG. 1 provides a synthetic pathway for forming the compounds having formula 4.

Examples for L include, but are not limited to, tBuNNCHCHNMe$_2$, $C_1$-$C_6$ alkyl, Cl, Br, or I. Additional examples for L and of compounds having formula $ML_o$ useful in the present embodiment and variations are set forth in U.S. Pat. No. 8,148,564; U.S. Pat. Pub. Nos. 20100239765; 20120058270; and 20130164456; PCT Appl. Nos. PCT/US12/40892 and PCT/US13/45144; and U.S patent application Ser. Nos. 13/493,560, 13/709,564, and 13/765,981; the entire disclosures of these documents are hereby incorporated by reference.

In example from U.S. Pat. Pub. No. 2012/0058270, $ML_o$ is also described by formula 5:

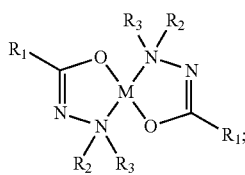

or geometric isomers thereof.

In the context of these compounds, geometric isomers include, but are not limited to, isomers in which the ligand atoms attaching to M are arranged in a tetrahedral configuration, a square planar configuration, or configurations intermediate between tetrahedral and square planar. In some geometric isomers, the O atoms attaching to M may be proximate (e.g., cis) or distant (e.g., trans). Examples for geometric isomers include, but are not limited to:

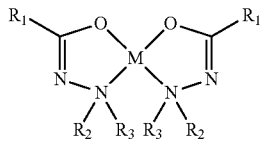

$R_1$, $R_2$, $R_3$ are each independently hydrogen, $C_1$-$C_{12}$ alkyl or $C_6$-$C_{12}$ aryl, Si(R$_6$)$_3$, or Ge(R$_6$)$_3$ and M is a transition metal. In a refinement of the compound described by formula 5, $R_1$, $R_2$, and $R_3$ are each independently hydrogen, methyl, ethyl, n-propyl, isopropyl, n-butyl, t-butyl, or sec-butyl. In another refinement, M is Ti, V, Cr, Mn, Fe, Co, Ni, Cu, Zn, Al, a second row transition metal or a third row transition metal. In another refinement of the compound described by formula 5, M is Cu, Ni, Co, Cr, Mn, or Fe. In yet another refinement of the compound described by formula 5, M is Cu, Ni, Co, or Cr.

In another example from U.S. Pat. Pub. No. 2012/0058270, $ML_o$ is also described by formula 6:

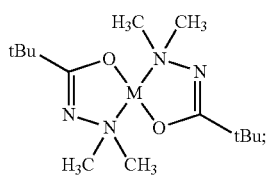

or geometric isomers thereof.

In the context of these compounds, geometric isomers include, but are not limited to, isomers in which the ligand atoms attaching to M are arranged in a tetrahedral configuration, a square planar configuration, or configurations intermediate between tetrahedral and square planar. In some geometric isomers, the O atoms attaching to M may be proximate (e.g., cis) or distant (e.g., trans). M is a transition metal. In another refinement, M is Ti, V, Cr, Mn, Fe, Co, Ni, Cu, Zn, Al, a second row transition metal or a third row transition metal. In another refinement of the compound described by formula 6, M is Cu, Ni, Co, Cr, Mn, or Fe. In yet another refinement of the compound described by formula 6, M is Cu, Ni, Co, or Cr.

In another example from U.S. Pat. Pub. No. 2012/0058270, $ML_o$ is also described by formula 7:

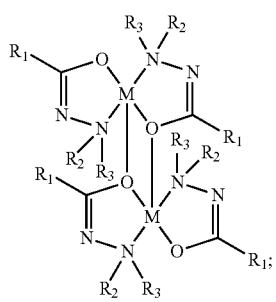

or geometric isomers thereof.

In the context of these compounds, geometric isomers include, but are not limited to, isomers in which the ligand atoms attaching to M are arranged in a tetrahedral configuration, a square planar configuration, or configurations intermediate between tetrahedral and square planar. In some geometric isomers, the O atoms attaching to M may be proximate (e.g., cis) or distant (e.g., trans). $R_1$, $R_2$, $R_3$ are each independently hydrogen, $C_1$-$C_{12}$ alkyl or $C_6$-$C_{12}$ aryl, Si(R$_6$)$_3$, or Ge(R$_6$)$_3$ and M is a transition metal. In another refinement, M is Ti, V, Cr, Mn, Fe, Co, Ni, Cu, Zn, Al, a second row transition metal or a third row transition metal. In a refinement of the compound described by formula 7, $R_1$, $R_2$, $R_3$ are each independently hydrogen, methyl, ethyl, n-propyl, isopropyl, n-butyl, t-butyl, or sec-butyl. In another refinement of the compound described by formula 7, M is Mn or Fe.

In another example from U.S. Pat. Pub. No. 2012/0058270, $ML_o$ is also described by formula 8:

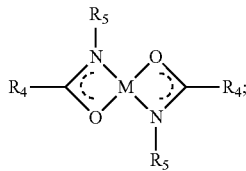

8 or geometric isomers thereof.

In the context of these compounds, geometric isomers include, but are not limited to, isomers in which the ligand atoms attaching to M are arranged in a tetrahedral configuration, a square planar configuration, or configurations intermediate between tetrahedral and square planar. In some geometric isomers, the O atoms from different ligands attaching to M may be proximate (e.g., cis) or distant (e.g., trans). Examples for geometric isomers include, but are not limited to:

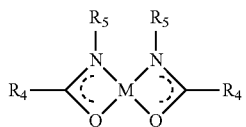

$R_4$ and $R_5$ are each independently hydrogen, $C_1$-$C_{12}$ alkyl or $C_6$-$C_{12}$ aryl, $Si(R_6)_3$, or $Ge(R_6)_3$ and M is a transition metal. In a refinement of the compound described by formula 8, $R_4$ and $R_5$ are each independently hydrogen, methyl, ethyl, n-propyl, isopropyl, n-butyl, t-butyl, or sec-butyl. In another refinement, M is Ti, V, Cr, Mn, Fe, Co, Ni, Cu, Zn, Al, a second row transition metal or a third row transition metal. In another refinement, M is Cu, Ni, Co, Cr, Mn, or Fe. In yet another refinement of the compound described by formula 8, M is Cu, Ni, Co, or Cr.

In another example from U.S. Pat. Pub. No. 2012/0058270, $ML_o$ is also described by formula 9:

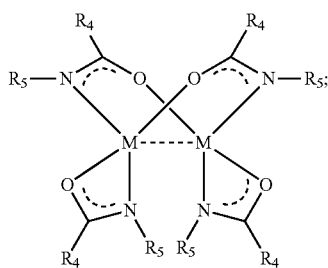

9 or geometric isomers thereof,

In the context of these compounds, geometric isomers include, but are not limited to, isomers in which the ligand atoms attaching to M are so that the O atoms attaching to M are proximate (e.g., cis) or distant (e.g., trans). Examples of geometric isomers for compounds having formula 9 include, but are not limited to:

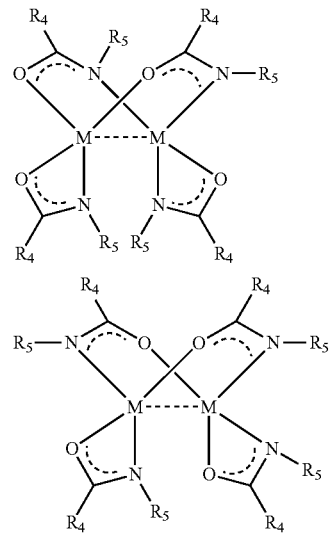

$R_4$ and $R_5$ are each independently hydrogen, $C_1$-$C_{12}$ alkyl or $C_6$-$C_{12}$ aryl, $Si(R_6)_3$, or $Ge(R_6)_3$ and M is a transition metal. In a refinement of the compound described by formula 9, $R_4$ and $R_5$ are each independently hydrogen, methyl, ethyl, n-propyl, isopropyl, n-butyl, t-butyl, iso-butyl or sec-butyl. The - - - between M is absent, a single bond, or a multiple bond. In another refinement of the compound described by formula 9, M is Ti, V, Cr, Mn, Fe, Co, Ni, Cu, Zn, Al, a second row transition metal or a third row transition metal. In another refinement of the compound described by formula 9, M is Cu, Ni, Co, Cr, Mn, or Fe. In yet another refinement of the compound described by formula 9, M is Cu, Ni, Co, or Cr.

In another example from U.S. Pat. Pub. No. 2012/0058270, $ML_o$ is also described by formula 10:

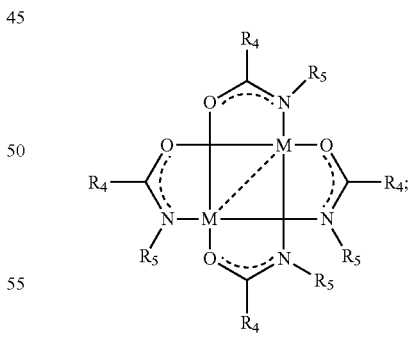

10 or geometric isomers thereof;

In the context of these compounds, geometric isomers include, but are not limited to, isomers in which the ligand atoms attaching to M are so that the O atoms attaching to M are proximate (e.g., cis) or distant (e.g., trans). Examples of geometric isomers for compounds having formula 10 include, but are not limited to:

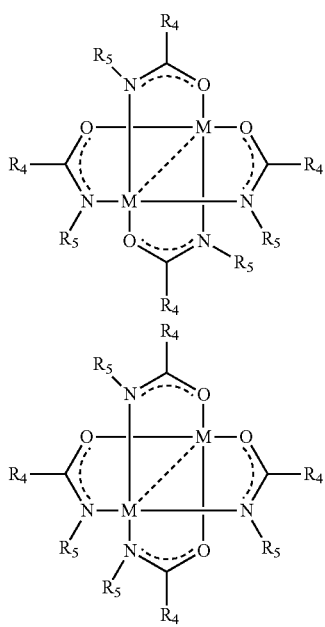

$R_4$ and $R_5$ are each independently hydrogen, $C_1$-$C_{12}$ alkyl or $C_6$-$C_{12}$ aryl, $Si(R_6)_3$, or $Ge(R_6)_3$ and M is a transition metal. In a refinement of the compound described by formula 10, $R_4$ and $R_5$ are each independently hydrogen, methyl, ethyl, n-propyl, isopropyl, n-butyl, t-butyl, iso-butyl or sec-butyl. The - - - between M is absent, a single bond, or a multiple bond. In another refinement of the compound described by formula 10, M is Ti, V, Cr, Mn, Fe, Co, Ni, Cu, Zn, Al, a second row transition metal or a third row transition metal. In another refinement of the compound described by formula 10, M is Cu, Ni, Co, or Cr.

From PCT Application No. PCT/US11/48792, examples of $ML_o$ include compounds having formula 11:

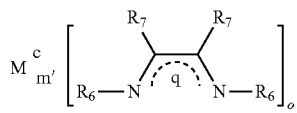

11 wherein:
M is a transition metal;
c is the formal charge of M (typically, c is 0, 1+, 2+, or 3+);
q is the formal charge of the ligand within the brackets (typically, 0, 1−, or 2−)
m' is an integer (typically, m' is 1);
o is an integer such that the overall formal charge of the compound having formula 11 is 0 (typically, o is 1, 2, or 3);
$R_6$ is $C_1$-$C_{12}$ alkyl, amine, or $C_6$-$C_{18}$ aryl; and
$R_7$ is hydrogen, $C_1$-$C_{10}$ alkyl, $C_6$-$C_{18}$ aryl, amino, $C_1$-$C_{12}$ alkylamino, or $C_2$-$C_{24}$ dialkylamino. In a refinement of the compound described by formula 11, M is Ti, V, Cr, Mn, Fe, Co, Ni, Cu, Zn, Al, a second row transition metal or a third row transition metal.

From PCT Application No. PCT/US11/48792, examples of $ML_o$ include compounds having formula 12:

12 wherein
M is a transition metal;
m' is an integer (typically, m' is 1);
o is an integer (typically, o is 1, 2, or 3);
$R_6$ is $C_1$-$C_{12}$ alkyl, amino (i.e., —$NH_2$), or $C_6$-$C_{18}$ aryl; and
$R_7$ is hydrogen, $C_1$-$C_{10}$ alkyl, $C_6$-$C_{18}$ aryl, amino, $C_1$-$C_{12}$ alkylamino, or $C_2$-$C_{22}$ dialkylamino. In a refinement of the compound described by formula 12, M is Ti, V, Cr, Mn, Fe, Co, Ni, Cu, Zn, Al, a second row transition metal or a third row transition metal.

From PCT Application No. PCT/US11/48792, examples of $ML_o$ include compounds having formula 13:

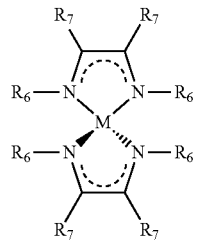

13 wherein
M is a transition metal;
$R_6$ is $C_1$-$C_{12}$ alkyl, amino (i.e., —$NH_2$), or $C_6$-$C_{18}$ aryl; and
$R_7$ is hydrogen, $C_1$-$C_{10}$ alkyl, $C_6$-$C_{18}$ aryl, amino, $C_1$-$C_{12}$ alkylamino, or $C_2$-$C_{22}$ dialkylamino. In a refinement of the compound described by formula 13, M is Ti, V, Cr, Mn, Fe, Co, Ni, Cu, Zn, Al, a second row transition metal or a third row transition metal.

From PCT Application No. PCT/US13/45144, examples of $ML_o$ include compounds having formula 14:

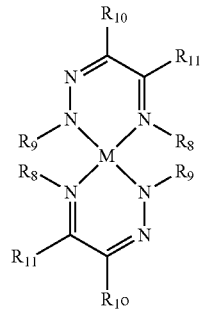

14 wherein:
M is a metal selected from groups 2 to 12 of the Periodic Table. In particular, M is Zn, Mg, Cr, Mn, Fe, Co, Ni, or Cu;
$R_8$ is $C_1$-$C_8$ alkyl, $C_5$-$C_{12}$ aryl, or $NR_{12}R_{13}$;
$R_9$ is $C_1$-$C_8$ alkyl;
$R_{10}$, $R_{11}$ are each independently hydrogen or $C_1$-$C_8$ alkyl; and
$R_{12}$, $R_{13}$ are each independently $C_1$-$C_8$ alkyl with the proviso that when M is Cr, $R_5$ is $C_2$-$C_8$ alkyl. In a refinement, when $R_8$ is $C_1$-$C_8$ alkyl, M is Zn, Mg, Cr, Mn, Fe, Co, or Ni, and when $R_8$ is $NR_{12}R_{13}$; M is Zn, Mg, Mn, Fe, Co, or Ni. In a refinement, $R_8$, $R_9$, $R_{10}$, $R_{11}$ are each independently methyl, ethyl, n-propyl, isopropyl, n-butyl, sec-butyl, isobutyl, t-butyl, or phenyl. In a particularly useful refinement, $R_9$ is t-butyl. In a variation of the compound having formula 14 when $R_8$ is $C_1$-$C_8$ alkyl, M is Cr, Mn, Fe, Co, or Ni, and when $R_8$ is N $R_{12}R_{13}$, M is Zn, Mg, Mn, Fe, Co, or Ni. In another variation, $R_8$ is $C_1$-$C_8$ alkyl and M is Zn, Mg, Cr, Mn, Fe, Co, or Ni. In still another variation, $R_8$ is N $R_{12}R_{13}$ and M is Zn, Mg, Mn, Fe, Co, or Ni.

From PCT Application No. PCT/US13/45144, examples of $ML_o$ include compounds having formula 15:

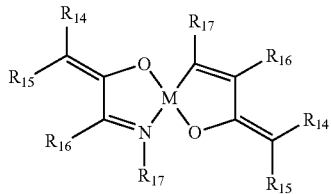

15 wherein:

M is a metal selected from groups 2 to 12 of the Periodic Table. In particular, M is Zn, Mg, Cr, Mn, Fe, Co, Ni, or Cu;
$R_{14}$, $R_{15}$, $R_{16}$ are each independently hydrogen, $C_1$-$C_8$ alkyl, $C_5$-$C_{12}$ aryl, or $C_5$-$C_{12}$ heteroaryl; and
$R_{17}$ is $C_1$-$C_8$ alkyl, $C_5$-$C_{12}$ aryl, or $C_5$-$C_{12}$ heteroaryl.
In a refinement, $R_{14}$, $R_{15}$, $R_{16}$, $R_{17}$ are each independently methyl, ethyl, n-propyl, isopropyl, n-butyl, sec-butyl, isobutyl, t-butyl, or phenyl. In a particularly useful refinement, $R_{10}$ is t-butyl.

From PCT Application No. PCT/US13/45144 (219), examples of $ML_o$ include compounds having formula 16:

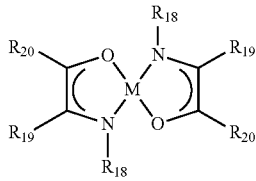

16

M is a metal selected from groups 2 to 12 of the Periodic Table. In particular, M is Zn, Mg, Cr, Mn, Fe, Co, Ni, or Cu;
$R_{18}$ is $C_1$-$C_8$ alkyl, $C_5$-$C_{12}$ aryl, or $C_5$-$C_{12}$ heteroaryl; and
$R_{19}$, $R_{20}$ are each independently hydrogen, $C_1$-$C_8$ alkyl, $C_5$-$C_{12}$ aryl, or $C_5$-$C_{12}$ heteroaryl. In a refinement, $R_{18}$, $R_{19}$, $R_{20}$ are each independently methyl, ethyl, n-propyl, isopropyl, n-butyl, sec-butyl, isobutyl, t-butyl, or phenyl. In a particularly useful refinement, $R_{11}$ is t-butyl.

From U.S. patent application Ser. No. 13/709,564, examples of $ML_o$ include compounds having formula 17:

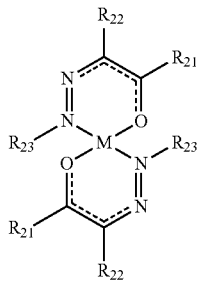

17 wherein
M is a metal selected from Groups 2 to 12 of the Periodic Table;
$R_{21}$ and $R_{22}$ are each independently H or $C_1$-$C_6$ alkyl; and
$R_{23}$ is H or H or $C_1$-$C_8$ alkyl. In a refinement, $R_{21}$, $R_{22}$ and $R_{23}$ are each independently methyl, ethyl, n-propyl, isopropyl, n-butyl, sec-butyl, isobutyl, or t-butyl. In another refinement, M is Cr, Mn, Fe, Co, or Ni.

Specific examples for $ML_o$ include compounds having Formulas 18-28:

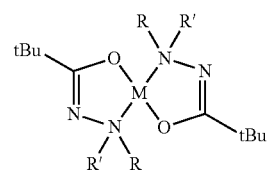

18 where M is Cu, Ni, Co, or Cr; and R, R' are $C_1$-$C_6$ alkyl;

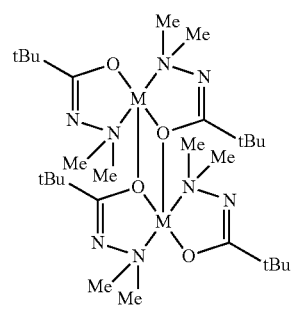

19 where M is Mn or Fe;

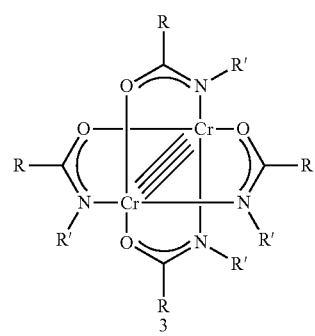

20 where R, R' are $C_1$-$C_6$ alkyl;

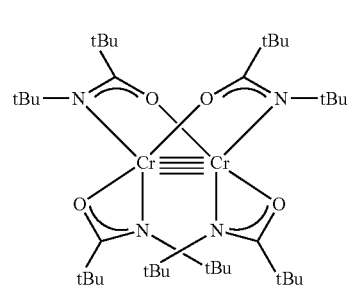

21

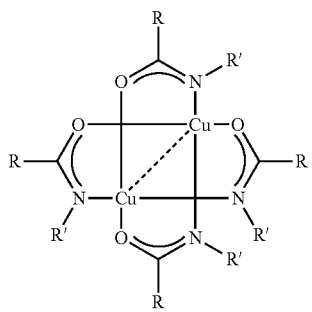

where R, R' are $C_1$-$C_6$ alkyl.

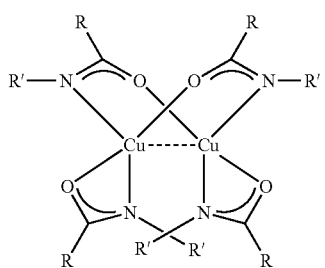

where R, R' are $C_1$-$C_6$ alkyl.

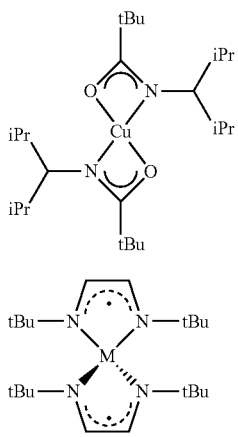

where M is Ni, Co, Fe, Mn, or Cr;

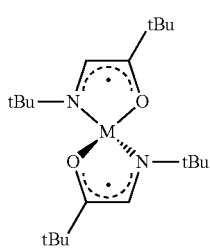

where M is Ni, Co, Fe, Mn, or Cr.

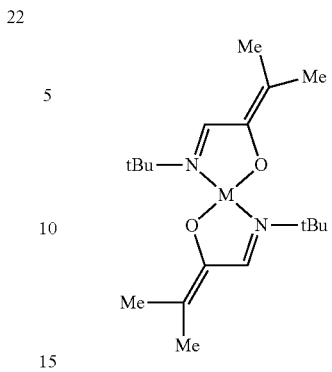

where M is Ni, Co, Fe, Mn, or Cr.

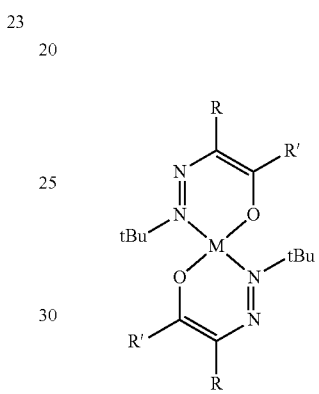

where M is Ni, Co, Fe, Mn, or Cr; and R, R' are $C_1$-$C_6$ alkyl.

In another variation, the compound having formula 1 is reacted with $ML_o$ to form a compound having formula 29:

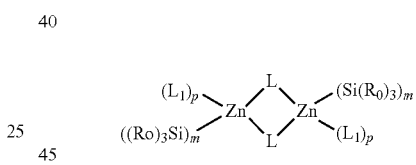

wherein:

M is Co, Ti, V, Mn, Fe, Cr, Ni, Cu, Zn, Al, a second transition metal, or a third row transition metal;

L is Cl, Br, or I;

$L_1$ is a neutral donor ligand;

R are each independently H, $C_1$-$C_6$ alkyl or $-Si(R'')_3$;

R'' are each independently H or $C_1$-$C_6$ alkyl;

m is 0 to 6;

o is an integer representing the number of ligands bonded to $ML_o$ and p is an integer from 0 to 6.

The compounds of the present variation form a metal (i.e., zero oxidation state) upon heating to temperatures from about 80 to 250° C. A particularly useful compound has formula 30:

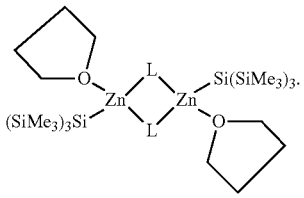

In another refinement, a method of forming a metal film by an atomic layer deposition process is provided. The method comprises a deposition which includes contacting the substrate with vapor of a compound having formulae 1, 2, 3, or 4 set forth above such that at least a portion of the vapor of the compound having formula 1, 2, 3, or 4 adsorbs or reacts with a substrate surface to form a modified surface. The deposition cycle further includes contacting the modified surface with a vapor of a compound having formula $ML_o$ to react and form at least a portion of the metal film. Typically, a vapor of a compound having formulae 1, 2, 3, or 4 is contacted with the compound having formula $ML_o$ at a temperature from about 50 to 400° C. The present reaction is used in an ALD process as set forth below.

Figure 2:
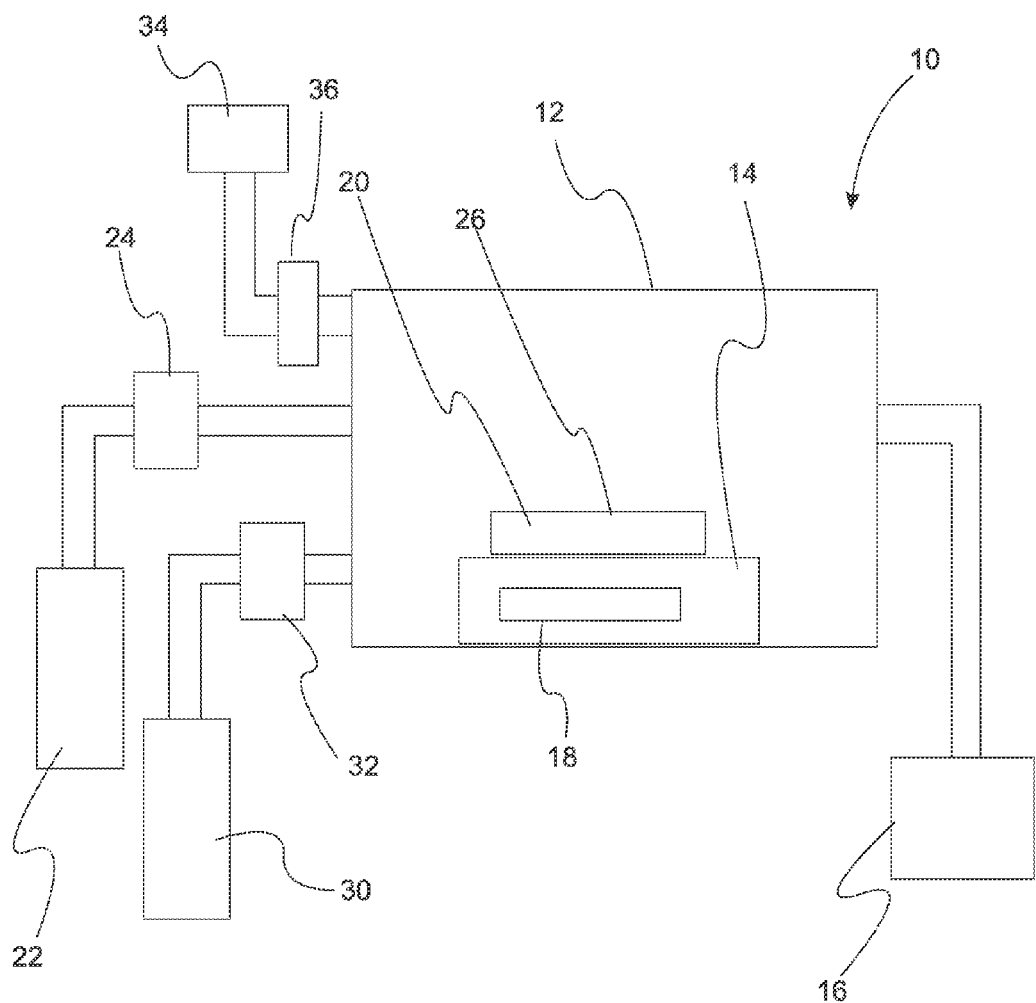
FIG. 2 is a schematic illustration of an ALD deposition system used in an embodiment of the present invention.

With reference to FIG. 2, deposition system 10 includes reaction chamber 12, substrate holder 14, and vacuum pump 16. Typically, the substrate is heated via heater 18. The method has a deposition cycle comprising contacting substrate 20 with a vapor of a metal-containing compound described by formula 1, 2, 3, or 4 as set forth above. In particular, the vapor is introduced from precursor source 22 into reaction chamber 12 for a predetermined pulse time. The pulse time is controlled via control valve 24. At least a portion of the vapor of the metal-containing compound modifies (e.g, adsorbs or reacts with) substrate surface 26 to form a modified surface. The method further comprises contacting the modified surface with a vapor of a compound having formula $ML_o$ as set forth above from source 30 for a predetermined pulse time. The pulse time is controlled via control valve 32. The compound having formula $ML_o$ causes the metal-containing compound to react and form at least a portion of the thin metal film on the surface of the substrate. The reduced pressure of chamber 12 is maintained by vacuum pump 16. In a variation, substrate 20 is first contacted with a vapor of $ML_o$ and then the vapor of a compound having formula 1, 2, 3, or 4.

In a variation of the present embodiment, the method further comprises removing at least a portion of the vapor of the metal containing compound having formula 1, 2, 3, or 4 that is lingering in the gas phase (i.e., has not adsorbed or reacted with the substrate) from the vicinity of the substrate before introducing the vapor of $ML_o$. The metal-containing compound and the compound having formula $ML_o$ are removed in purging steps by introducing a purge gas from purge source 34 into reaction chamber 12 for a predetermined purge time. The purge time is controlled by control valve 36.

In another variation, the method further includes at least one additional deposition cycle comprising sequentially contacting the substrate with the vapor of a metal-containing compound having formula 1, 2, 3, or 4 and then the vapor of the compound having formula $ML_o$. In some refinements, the substrate is contacted for a plurality of additional deposition cycles. For example, the substrate may be contacted with from 1 to several 5000 additional deposition cycles depending on the thickness of the film desired.

During film formation by the method of the present embodiment, the substrate temperature will be at a temperature suitable to the properties of the chemical precursor(s) and film to be formed. In a refinement of the method, the substrate is set to a temperature from about 0 to 1000° C. In another refinement of the method, the substrate has a temperature from about 50 to 450° C. In another refinement of the method, the substrate has a temperature from about 100 to 250° C. In still another refinement of the method, the substrate has a temperature from about 150 to 400° C. In another refinement of the method, the substrate has a temperature from about 200 to 300° C. For metal film growth by ALD, temperatures of <150° C. are best to avoid rough films due to balling up of the metals at higher temperatures Similarly, the pressure during film formation is set at a value suitable to the properties of the chemical precursors and film to be formed. In one refinement, the pressure is from about $10^{-6}$ Torr to about 760 Torr. In another refinement, the pressure is from about 0.1 millitorr to about 10 Torr. In still another refinement, the pressure is from about 1 to about 100 millitorr. In yet another refinement, the pressure is from about 1 to 20 millitorr.

Pulse times and purge times also depend on the properties of the chemical precursors and the geometric shape of the substrates. Thin film growth on flat substrates uses short pulse and purge times, but pulse and purge times in ALD growth on 3-dimensional substrates can be very long. Therefore, in one refinement, pulse times and purge times are each independently from about 0.0001 to 200 seconds. In another refinement, pulse and purge times are each independently from about 0.1 to about 10 seconds.

Synthesis of $[ZnCl(Si(SiMe_3)_3)(THF)]_2$ (31). A solution of $Zn[Si(SiMe_3)_3]_2$ (0.400 g, 0.715 mmol) and $ZnCl_2$ (0.097 g, 0.715 mmol) in THF (40 ml) was stirred at room temperature for 3 h. Volatile components were removed under reduced pressure to afford a white solid. The resultant solid was extracted with hexane (70 mL), filtered through a 2 cm pad of Celite, concentrated and left at −28° C. Complex 31 was isolated as colorless single crystals. (0.299 g, 99%): mp 140-142° C.; $^1$H NMR (benzene-$d_6$, 23° C., δ) 0.42 (s, 54H, Si—CH$_3$), 1.36 (t, 8H, THF) 3.76 (t, 8H, THF); $^{13}$C{$^1$H} NMR (benzene-$d_6$, 23° C., ppm) 4.03 (s, Si—CH$_3$), 25.21 (s, THF), 69.07 (s, THF). Anal. Calcd for $C_{26}H_{70}Cl_2O_2Si_8Zn_2$: C, 37.12; H, 8.39. Found: C, 36.89; H, 8.29.

Synthesis of $[ZnBr(Si(SiMe_3)_3)(THF)]_2$ (32). In a fashion similar to the preparation of 31, treatment of $Zn[Si(SiMe_3)_3]_2$ (0.400 g, 0.715 mmol) with $ZnBr_2$ (0.161 g, 0.715 mmol) in THF afforded 32 (0.275 g, 83%) as colorless single crystals after crystallization from hexane at −28° C.: mp 142-144° C.; $^1$H NMR (benzene-$d_6$, 23° C., δ) 0.41 (s, 54H, Si—CH$_3$), 1.32 (t, 8H, THF) 3.70 (t, 8H, THF); $^{13}$C{$^1$H} NMR (benzene-$d_6$, 23° C., ppm) 3.97 (s, Si—CH$_3$), 25.32 (s, THF), 69.01 (s, THF). Anal. Calcd for $C_{26}H_{70}Br_2O_2Si_8Zn_2$: C, 33.58; H, 7.59. Found: C, 31.93, 32.13; H, 6.94, 6.61.

Synthesis of $[ZnI(Si(SiMe_3)_3)(THF)]_2$ (33). In a fashion similar to the preparation of 31, treatment of $Zn[Si(SiMe_3)_3]_2$ (0.0366 g, 0.60 mmol) with $ZnI_2$ (0.192 g, 0.60 mmol) in THF afforded 33 (0.303 g, 99%) as colorless single crystals after crystallization from pentane at −28° C.: mp 160-162° C.; $^1$H NMR (benzene-$d_6$, 23° C., δ) 0.42 (s, 54H, Si—CH$_3$), 1.30 (t, 8H, THF) 3.66 (t, 8H, THF); $^{13}$C{$^1$H} NMR (benzene-$d_6$, 23° C., ppm) 3.96 (s, Si—CH$_3$), 25.36 (s, THF), 69.43 (s, THF). Anal. Calcd for $C_{26}H_{70}I_2O_2Si_8Zn_2$: C, 30.49; H, 6.89. Found: C, 30.00; H, 6.86.

Synthesis of $Zn(tBuNNCHCHNMe_2)_2$. A Schlenk flask was charged with 1-tert-butyl-5-dimethylamino-1,2,5-triazapentadiene (0.255 g, 1.50 mmol) and THF (30 mL). To the stirred solution at ambient temperature was slowly added potassium hydride (0.066 g, 1.65 mmol), and the solution was stirred for 4 h. A separate Schlenk flask was charged with $ZnCl_2$ (0.102 g, 0.75 mmol) and THF (30 mL). The potassium salt solution was then cannulated into the stirred solution of $ZnCl_2$ and the resultant mixture was stirred for 18 h. Volatile components were removed under reduced pressure to afford a bright yellow solid. The resultant solid was extracted with pentane (60 mL), filtered through a 2 cm pad of Celite, concentrated and left at $-28°$ C. to afford yellow single crystals (0.115 g, 38%): $^1$H NMR (benzene-$d_6$, 23° C., δ) 1.48 (s, 18H, $C(CH_3)_3$), 2.30 (s, 12H, $N(CH_3)_2$), 6.62 (d, 2H, NNCH), 6.68 (d, 2H, NCH); $^{13}C\{^1H\}$ NMR (benzene-$d_6$, 23° C., ppm) 30.26 (s, $C(CH_3)_3$), 45.78 (s, $C(CH_3)_3$), 61.28 (s, $N(CH_3)_2$), 112.86 (s, NCH), 141.32 (s, NNCH). Anal. Calcd for $C_{16}H_{34}N_8Zn$: C, 47.58; H, 8.49; N, 27.74. Found: C, 47.32; H, 8.48; N, 26.60.

Synthesis of $Zn(tBuNNCHCHNtBu)_2$. A Schlenk flask was charged with 1,5-di-tert-butyl-1,2,5-triazapentadiene (0.366 g, 2.00 mmol) and THF (30 mL). To the stirred solution at ambient temperature was slowly added potassium hydride (088 g, 2.2 mmol), and the solution was stirred for 4 h. A separate Schlenk flask was charged with $ZnCl_2$ (0.136 g, 1.00 mmol) and THF (30 mL). The potassium salt solution was cannulated into the stirred solution of $ZnCl_2$ and stirred for 18 h. Volatile components were removed under reduced pressure to afford a bright yellow solid. The resultant solid was extracted with hexane (80 mL) and afforded yellow crystals (0.362 g, 56%) upon sublimation at 140° C./0.05 Torr. (0.362 g, 56%): $^1$H NMR (benzene-$d_6$, 23° C., δ) 1.08 (s, 18H, $NNC(CH_3)_3$), 1.47 (s, 18H, $NC(CH_3)_3$), 6.74 (d, 2H, NNCH), 6.77 (d, 2H, NCH); $^{13}C\{^1H\}$ NMR (benzene-$d_6$, 23° C., ppm) 30.43 (s, $NNC(CH_3)_3$), 31.43 (s, $NC(CH_3)_3$), 56.86 (s, $NNC(CH_3)_3$), 62.02 (s, $NC(CH_3)_3$), 115.65 (s, NCH), 148.46 (s, NNCH). Anal. Calcd for $C_{20}H_{40}N_6Zn$: C, 55.87; H, 9.38; N, 19.55. Found: C, 55.61; H, 9.04; N, 19.29.

Synthesis of $Co[Si(SiMe_3)_3]_2$. A solution of $CoCl_2$ (0.117 g, 0.90 mmol) and $(THF)_3LiSi(SiMe_3)_3$ (0.848 g, 1.80 mmol) in diethyl ether (30 mL) was stirred at room temperature for 18 h. The volatiles were removed under reduced pressure afforded a black solid. $^1$H NMR (benzene-$d_6$, 23° C., δ) 0.32 (s, broad 54H, $Si(CH_3)_3$).

Synthesis of $Ni[Si(SiMe_3)_3]_2$. A solution of $NiCl_2 \cdot CH_3CN$ (0.154 g, 0.90 mmol) and $(THF)_3LiSi(SiMe_3)_3$ (0.848 g, 1.80 mmol) in THF (30 mL) was stirred at room temperature for 18 h. The volatiles were removed under reduced pressure afforded a dark brown solid. $^1$H NMR (benzene-$d_6$, 23° C., δ) 0.25 (s, 54H, $Si(CH_3)_3$).

Thermolysis of $[ZnBr(Si(SiMe_3)_3)(THF)]_2$. A 10 mL pressure flask was charged with $[ZnBr(Si(SiMe_3)_3)(THF)]_2$ (0.356 g, 0.387 mmol) and hexamethylbenzene (0.32 g, 0.194 mmol) as an internal standard, immersed in an oil bath, and heated at 225° C. for 4 hours to afford zinc metal (99%), which was identified by powder X-ray diffraction. The organic product was identified as $BrSi(SiMe_3)_3$ (77%) by $^1$H NMR spectroscopy after extraction with hexane, filtration, and removal of the volatile components: (benzene-$d_6$, 23° C., δ) 0.23 (s, 27H, $Si(CH_3)_3$). The yield was determined by integration versus the hexamethylbenzene methyl resonance.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for forming a metal, the method comprising:
   contacting a compound having formulae 1 or a surface modified with the compound having formula 1 with a compound having formula $ML_o$ to form a metal:

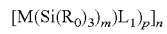

wherein
   M is Ti, V, Cr, Mn, Fe, Co, Ni, Cu, Zn, Al, a second row transition metal or a third row transition metal;
   $R_0$ are each independently H or $C_1$-$C_6$ alkyl;
   R" are each independently H or $C_1$-$C_6$ alkyl;
   m is an integer from 1 to 6;
   n is a number representing formation of aggregates or polymeric material;
   L is a ligand;
   $L_1$ is a neutral donor ligand;
   p is an integer from 0 to 6; and
   o is an integer representing the number of ligands bonded to $ML_o$.

2. The method of claim 1 wherein n is a number from 1 to 1000.

3. The method of claim 1 wherein n is a number from 1 to 3.

4. The method of claim 1 wherein the compound having formula 1 is:

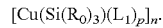

5. The method of claim 1 wherein L is tBuNNCHCHNMe$_2$.

6. The method of claim 1 wherein $R_0$ is methyl, ethyl, n-propyl, isopropyl, n-butyl, sec-butyl, isobutyl, or t-butyl.

7. The method of claim 1 wherein $ML_o$ is:

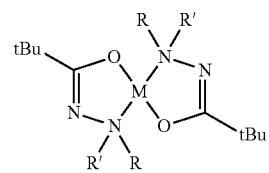

where M is Cu, Ni, Co, or Cr; and
R, R' are each independently $C_1$-$C_6$ alkyl.

8. The method of claim 1 wherein $ML_o$ is:

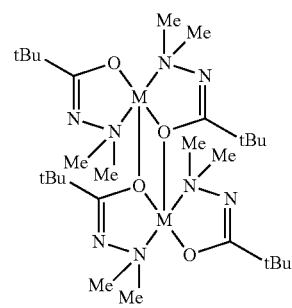

where M is Mn or Fe.

9. The method of claim 1 wherein $ML_o$ is:

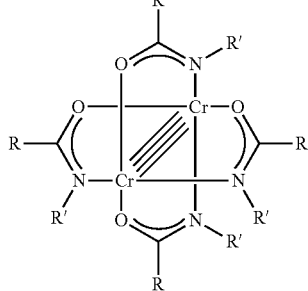

where R, R' are each independently $C_1$-$C_6$ alkyl.

10. The method of claim 1 wherein $ML_o$ is:

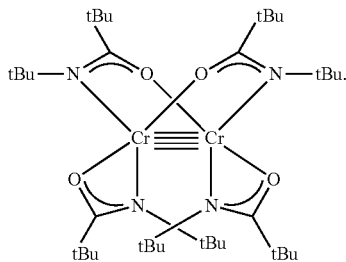

11. The method of claim 1 wherein $ML_o$ is:

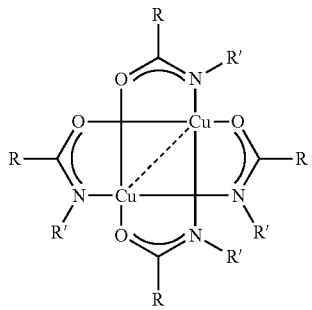

where R, R' are each independently $C_1$-$C_6$ alkyl.

12. The method of claim 1 wherein $ML_o$ is:

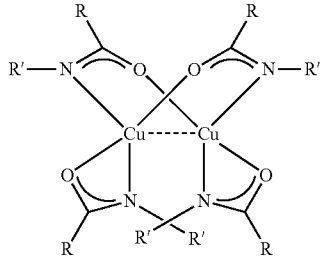

where R, R' are each independently $C_1$-$C_6$ alkyl.

13. The method of claim 1 wherein $ML_o$ is:

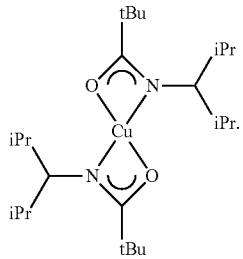

14. The method of claim 1 wherein $ML_o$ is:

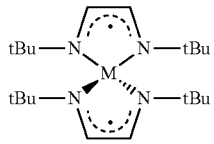

where M is Ni, Co, Fe, Mn, or Cr.

15. The method of claim 1 wherein $ML_o$ is

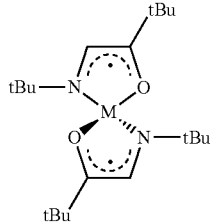

where M is Ni, Co, Fe, Mn, or Cr.

16. The method of claim 1 wherein $ML_o$ is:

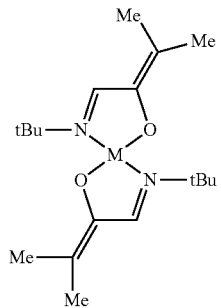

where M is Ni, Co, Fe, Mn, or Cr.

17. The method of claim 1 wherein $ML_o$ is:

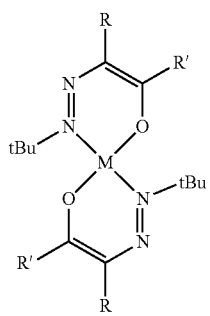

where M is Ni, Co, Fe, Mn, or Cr; and
R, R' are each independently $C_1$-$C_6$ alkyl.

18. The method of claim 1 wherein the compound having formula 1 is reacted with $ML_o$ in the liquid phase.

19. The method of claim 1 wherein the compound having formula 1 is reacted with $ML_o$ in a deposition cycle comprising
   a) contacting a substrate with a vapor of the compound having formula 1; and
   b) contacting the substrate with a vapor of $ML_o$.

20. The method of claim 19 wherein the deposition cycle is repeated 1 to 5000 times.

21. The method of claim 19 wherein the substrate is at a temperature from about 0 to 1000° C.

22. The method of claim 19 wherein the substrate is contacted with a purge gas after step a) and prior to step b) and after step b).

23. The method of claim 1 wherein the compound having formula 1 is reacted with $ML_o$ in a deposition cycle comprising
   a) contacting a substrate with a vapor of $ML_o$; and
   b) contacting the substrate with a vapor of the compound having formula 1.

24. The method of claim 23 wherein the deposition cycle is repeated 1 to 5000 times.

25. The method of claim 23 wherein the substrate is at a temperature from about 0 to 1000° C.

26. The method of claim 23 wherein the substrate is contacted with a purge gas after step a) and prior to step b) and after step b).

27. The method of claim 1 wherein L is $C_{1-6}$ alkyl, Cl, Br, or I.

28. The method of claim 27 wherein M is Zn.

29. The method of claim 1 wherein the compound having formula 1 reacts with $ML_o$ to form a compound having formula 29 prior to formation of metal:

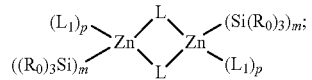

and
L is Cl, Br, or I.

30. The method of claim 29 wherein the compound having formula 1 reacts with $ML_o$ to form a compound having formula 30 prior to formation of metal:

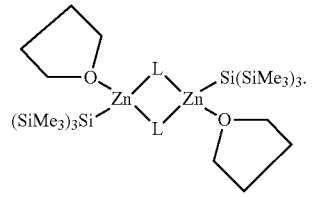

31. The method of claim 1 wherein M is T, Cr, Mn, Fe, Co, Ni, Cu, Zn, Al, Y, Zr, Nb, Mo, Tc, Ru, Rh, Pd, Ag, Hf, Ta, W, Re, Os, Ir, Pt, or Au.

32. The method of claim 1 wherein M is Ti, V, Cr, Mn, Fe, Co, Ni, Cu, Zn, or Al.

* * * * *